US00RE35247E

United States Patent [19]

Cyrus, Jr. et al.

[11] E Patent Number: Re. 35,247

[45] Reissued Date of Patent: May 21, 1996

[54] BIOCATALYTIC PRODUCTION OF PHENOLIC RESINS WITH RAMPED PEROXIDE ADDITION

[75] Inventors: William L. Cyrus, Jr., Ray; Alexander R. Pokora, Pickerington, both of Ohio

[73] Assignee: The Mead Corporation

[21] Appl. No.: 270,867

[22] Filed: Jul. 5, 1994

Related U.S. Patent Documents

Reissue of:

[64] Patent No.: 5,278,055
Issued: Jan. 11, 1994
Appl. No.: 895,905
Filed: Jun. 9, 1992

[51] Int. Cl.[6] ..... C12P 7/22; C12P 7/32; C12N 9/04; C12N 9/08

[52] U.S. Cl. ..... 435/156; 435/132; 435/190; 435/192

[58] Field of Search ..... 435/156, 132, 435/190, 192

[56] References Cited

U.S. PATENT DOCUMENTS

| | | | |
|---|---|---|---|
| 4,657,856 | 4/1987 | Terada et al. | 435/192 |
| 4,900,671 | 2/1990 | Pokora et al. | 435/156 |
| 5,110,740 | 5/1992 | Pokora et al. | 435/132 |
| 5,112,752 | 5/1992 | Johnson et al. | 435/192 |
| 5,147,793 | 9/1992 | Johnson et al. | 435/156 |

*Primary Examiner*—Herbert J. Lilling
*Attorney, Agent, or Firm*—Thompson Hine & Flory

[57] ABSTRACT

A process for preparing a phenolic resin which comprises preparing a reaction medium containing a phenol and a peroxidase enzyme and adding a solution of a peroxide to said medium, said peroxide being added to said medium at a rate which decreases from an initial rate of about 2 to 3 millimolar/min as the amount of phenol in said medium decreases such that the concentration of peroxide does not exceed about 12 millimolar.

6 Claims, No Drawings

BIOCATALYTIC PRODUCTION OF PHENOLIC RESINS WITH RAMPED PEROXIDE ADDITION

Matter enclosed in heavy brackets [ ] appears in the original patent but forms no part of this reissue specification; matter printed in italics indicates the additions made by reissue.

The present invention is an improvement in the biocatalytic processes for producing phenolic resins described in U.S. Pat. No. 4,900,671 and U.S. application Ser. No. 07/599,584 filed Oct. 18, 1990 now U.S. Pat. No. 5,147,793.

U.S. Pat. No. 4,900,671 commonly assigned to The Mead Corporation discloses a method for preparing a phenolic resin which comprises preparing a solution of a phenol in a water miscible or a water-immiscible solvent and an aqueous solution of a peroxidase or oxidase enzyme, mixing the two solutions and adding a peroxide or oxygen. The preferred method described in this patent makes use of horseradish peroxidase. Hydrogen peroxide is added to the system and reaction occurs on the enzyme. U.S. application Ser. No. 07/599,584 now U.S. Pat. No. 5,147,793 discloses that soybean peroxidase and other plant peroxidases can be used in this method.

SUMMARY OF THE INVENTION

In the biocatalytic processes described above, the peroxide is consumed and converted into free radicals by the enzyme catalyst. As the reaction proceeds, monomeric phenol is converted to resin product. In the later stages of the reaction, the concentration of monomeric phenol falls and the consumption of the peroxide slows to a point at which an excess of peroxide is present. The excess peroxide is believed to interfere with the reaction of the remaining phenol by inhibiting the catlayst or terminating chain transfer. This results in poor reaction and production efficiencies as reflected in higher concentrations of residual monomer than are desirable in the resin and lower molecular weight resins.

In accordance with the present invention, the peroxide addition is ramped, i.e., high concentrations of peroxide are used at the beginning of the reaction when high concentrations of monomeric phenol are present and lower concentrations of peroxide are used in later stages of the reaction when higher peroxide concentrations would lead to premature termination of the reaction.

Accordingly, one manifestation of the present invention is a process for preparing a phenolic resin which comprises preparing a reaction medium containing an unreacted phenol and a peroxidase enzyme and adding a solution of a peroxide to said medium, said solution being added to said reaction medium at a rate which decreases from an initial rate as the concentration of said unreacted phenol in said medium decreases.

DEFINITIONS

The term "phenolic resin" as used herein includes phenolic dimers and trimers as well as oligomers and higher molecular weight species.

A "unit" of peroxidase means the amount of peroxidase which produces a change of 12 absorbance units measured at 1 cm pathlength in one minute at 420 nm when added to a solution containing 100 mM potassium phosphate, 44 mM pyrogallol and 8 mM hydrogen peroxide and having a pH of 6 (Sigma Chemical Co. Peroxidase Bulletin).

DETAILED DESCRIPTION

A variety of peroxidases can be used in the present invention. The most preferred peroxidases are soybean and horseradish peroxidases. However, peroxidases from other legumes are also useful such as peroxidases from peas, guar beans, garbanzo beans, and runner beans. It is also believe that peroxidases from rice and certain malvaceous plants, such as cotton, may be useful.

Peroxidases useful herein are commercially available. Being water soluble they are easily harvested by homogenizing the protein source with water, filtering the homogenate, and retaining the filtrate. The filtrate is treated to remove proteinaceous and lipophilic impurities by adding to the filtrate a solution of a protein fixative or a detergent and forcing the enzyme to precipitate by the addition of a non-solvent for the peroxidase such as acetone or isopropanol. Useful purification techniques are described in the above-referenced patent application.

Legume hulls such as soybean hulls are biocatalytically active and can be used directly in some cases. It is not clear whether the peroxidase is being extracted by the reaction solvent medium or whether the peroxidase reacts similar to an immobilized enzyme. A combination of both mechanisms may occur.

The amount of hulls used will depend on their reactivity. For preparation of soybean hulls and suggested reaction amounts see the above-referenced patent application.

The amount of the enzyme used to make the phenolic resin will depend on its activity. The enzyme is not consumed in the reaction but gradually loses activity during the course of reaction. For practical purposes, the enzyme can be reacted in an amount of about 500 to 500,000 and more typically 1000 to 5000 units per 100 grams phenol.

The peroxide used is typically hydrogen peroxide, but other peroxides are also useful. Examples of other potentially useful peroxides include methyl peroxide, ethyl peroxide, etc.

The peroxide is reacted in a total amount of about 0.1 to 2.5 moles per mole phenol (or other oxidizable substrate) and, more typically, about 0.1 to 1.0 mole per mole phenol. Depending upon its nature, it is reacted neat or as a solution. In the preferred embodiments, hydrogen peroxide, is dissolved in water in a concentration of about 1 mM to 10 M and added to the reaction medium as described next.

The initial rate of addition (moles/min) of the peroxide solution is set at about twice the average reaction rate. Typically, the peroxide is initially added at a rate of about 2 to 3 millimolar/min. Thereafter, the reaction rate of the peroxide is downwardly adjusted for the decrease in the rate of reaction which accompanies the reaction of the phenol and the lower phenol concentrations. The rate of downward adjustment is controlled such that the peroxide concentration does not exceed 3 to 12 and more preferably about 3 to 5 millimolar.

The phenols can be reacted in a water-miscible or a water-immiscible solvent. Representative examples of useful water-immiscible solvents include hexane, trichloromethane, methyl ethyl ketone, ethyl acetate, and butanol. Examples of useful water-miscible solvents include ethanol, methanol, dioxane, tetrahydrofuran (THF), dimethyl formamide, methyl formate, acetone, n-propanol, isopropanol, ethanol, t-butyl alcohol. The reaction is typically carried out at phenol concentrations of about 1 to 100 g per 100 ml solvent.

A number of different procedures may be used to react the phenol or other oxidizable substrate. Solutions of the phenol and enzyme may be individually prepared and metered into a reaction vessel, or solutions of the phenol and enzyme may be pre-mixed. Alternatively, the enzyme and the phenol may be dissolved in a common solvent. However, the preferred reaction system is a mixture of water and a solvent.

The organic-aqueous system formed upon mixing the phenol, enzyme and peroxide may contain water and an organic solvent in a volumetric ratio (water:organic) in the range of about 1:10 to 10:1, more typically, 1:2 to 2:1. The most preferred ratio will vary with the solubility characteristics of the phenolic monomer(s) that is (are) polymerized and the resin which is produced.

Reaction temperatures will vary with the substrate and the enzyme. Enzymes are generally quite temperature sensitive and a temperature is selected which does not denature the enzyme, lower its reactivity or otherwise inhibit the reaction. The reaction of the phenol proceeds at room temperature, but temperatures of about 0° to 70° C. can be used. The enzymes can lose their activity if the reaction temperature becomes much higher. However, some latitude exists, depending upon the solvent system which is used. Certain solvents appear to stabilize the enzyme and thereby permit the use of higher temperatures. There is evidence in the literature that temperatures up to 100° C. may be useful with some peroxidases.

The activity of peroxidases is pH dependent. The oxidative reactions are typically carried out at a pH in the range of 4 to 12 and, preferably, 4 to 9, and, more preferably, about 6. A pH may be selected at which the enzyme is highly active. This will vary with the nature of the enzyme and its source. Buffers can be used to maintain pH, but are not usually required. One example of a useful buffer is a potassium phosphate buffer.

While reference is herein made to the bulk pH of the reaction system, those skilled in the art will appreciate that it is the pH in the micro-environment of the enzyme that is critical. Thus, where the phenol is dissolved in a water-immiscible solvent and the enzyme solution is dispersed in the solution of the phenol, it is the pH of the enzyme solution which is critical.

Phenolic resins prepared in accordance with the present invention are useful in a variety of applications depending on the nature of the phenol and the molecular weight distribution of the resin. Among other factors affecting molecular weight are solvent selection, phenol selection, and reaction conditions. The resins are often mixtures of dimers, trimers, and higher molecular weight oligomers. Phenolic resins useful as developers in recording materials such as carbonless copy paper, heat-sensitive recording paper, electrothermographic recording paper are preferably para-substituted and may range from about 500 to 5000 in molecular weight. The phenols used in adhesives need not be para-substituted. These resins typically range from about 1000 to 15,000 in molecular weight but molecular weights up to at least 30,000 are attainable.

Phenols which are preferred for reaction in the present invention are represented by the Formula (I):

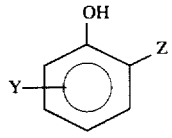

(1)

wherein Y and Z are selected from the group consisting of a hydrogen atom, a halogen atom, an alkyl group, an alkoxy group, an aryl group, an allyl group, a phenylalkyl group, a —COOR group, a —$NR^1R^2$ group, where R represents a hydrogen atom or a lower alkyl group, and $R^1$ and $R^2$ represent a hydrogen atom, an alkyl group, or a phenylalkyl group or Z in conjunction with the adjacent meta position forms a condensed benzene ring. Since polymerization proceeds via the ortho or para positions, when Y is at the ortho or para position, at least one of Y and Z must be a hydrogen atom or Z must form a condensed benzene ring. Y is preferably para to the phenolic hydroxyl group. U.S. Pat. No. 4,900,671 contains a discussion of phenolic substitution which may be used in this invention.

Specific examples of phenols which can be polymerized in accordance with the process of the present invention are phenol, 4-t-butylphenol, 4-n-butylphenol, 4-ethylphenol, cresol, p-phenylphenol, p-octylphenol, p-nonylphenol, p-hydroxybenzoate, bisphenol A, etc.

In addition to being useful in reacting phenols, the method of this invention is also useful in the reaction of other oxidizable substrates such as aromatic amines. Examples of other oxidizable substrates are disclosed in the above-referenced patent application.

The invention is illustrated in more detail by the following non-limiting examples.

COMPARATIVE EXAMPLE 1800 ml of acetone is added to a 5000 ml jacketed, 3-necked, round bottom flask. The jacket is used to maintain the temperature of the flask at 15° C. The acetone is mixed with a mechanical stirrer at 300 RPM and 500 g bisphenol A is added After the bisphenol A is dissolved, 1078 ml distilled water is added with 122.0 ml of a horseradish peroxidase enzyme solution containing 25,000 total purpurogallin units. A 15% hydrogen peroxide solution is then added using a peristaltic pump at a constant rate of 1 ml/min. until 500 ml have been added. A resin containing 23.43% residual monomer and having Mn=4410 and Mw=7992 was obtained.

EXAMPLE 1

360 ml of acetone is placed in a 1000 ml jacketed, 3-necked, round bottom flask. The jacket is used to maintain the temperature of the flask at 15° C. The acetone is mixed using a mechanical stirrer at 300 RPM and 100 g bisphenol A is added. After the bisphenol A is dissolved, 215 ml distilled water and 25 ml horseradish peroxidase enzyme solution containing 5,000 total purpurogallin units are added. A 15% hydrogen peroxide solution is metered into the reaction medium using a peristaltic pump at a ramped rate starting at 0.6 ml/min. and decreasing at a constant ramped rate until the rate is 0.0 ml/min. after 6 hrs. A total of 107 ml hydrogen peroxide solution is added. The resin contained less than 1% residual monomer and had Mn=4966 and Mw=9097.

EXAMPLE 2

302 ml of isopropyl alcohol was added to a 1000 ml jacketed, 3-necked, round bottom flask. The jacket was maintained at a temperature of 55° C. The alcohol was stirred with a mechanical stirrer at 350 RPM and 100 g t-butylphenol was added. After the phenol dissolved 285.2 ml distilled water and 16.8 ml soy enzyme soluton containing 2515 total purpurogallin units was added. When the contents of the flask reached 50° C the peroxide addition was begun. 35% hydrogen peroxide solution was added by use of a computer controlled peristaltic pump at a ramped rate over a 2 hour period. The initial rate was set to 0.76 ml/min. and at the end of 2 hours the rate was zero.

Having described the invention in detail and by reference to preferred embodiments thereof, it will be apparent that modifications and variations are possible without departing from the scope of the invention defined in the appended claims.

What is claimed is:

1. A process for preparing a phenolic resin which comprises preparing a reaction medium containing a phenol and a peroxidase enzyme and adding a solution of a peroxide to said medium, said peroxide being added to said medium at a rate which decreases from an initial rate [of about 2 to 3 millimolar/min] as the amount of phenol in said medium decreases such that the concentration of peroxide *in said medium* does not exceed about 12 millimolar.

2. The process of claim 1 wherein said medium is a mixture of water and an organic solvent.

3. The process of claim 2 wherein said organic solvent is a water-miscible solvent.

4. The process of claim 2 wherein said peroxidase is horseradish peroxidase or soybean peroxidase.

5. The process of claim 4 wherein said phenol is present in said medium in a concentration of 1 to 100 g/100 ml

6. The process of claim 5 wherein said rate decreases such that the concentration of peroxide in said reaction medium does not exceed about 3 to 12 millimolar.

* * * * *